United States Patent
Du-Nour

(10) Patent No.: US 6,762,838 B2
(45) Date of Patent: Jul. 13, 2004

(54) METHOD AND APPARATUS FOR PRODUCTION LINE SCREENING

(75) Inventor: Ofer Du-Nour, Timrat (IL)

(73) Assignee: Tevet Process Control Technologies Ltd., Yokneam Moshava (IL)

( * ) Notice: Subject to any disclaimer, the term of this patent is extended or adjusted under 35 U.S.C. 154(b) by 89 days.

(21) Appl. No.: 09/895,333

(22) Filed: Jul. 2, 2001

(65) Prior Publication Data

US 2003/0002032 A1 Jan. 2, 2003

(51) Int. Cl.$^7$ ............................................. G01B 11/06
(52) U.S. Cl. ..................... 356/382; 356/381; 356/328; 356/345; 356/346; 250/559.27; 250/559.28
(58) Field of Search ................................ 356/345, 346, 356/328, 381, 382, 630, 631, 632, 633, 634; 250/559.27, 559.28, 559.19, 559.01, 559.22

(56) References Cited

U.S. PATENT DOCUMENTS

| | | | | |
|---|---|---|---|---|
| 4,623,254 A | * | 11/1986 | Imose | ........................ 356/381 |
| 4,785,336 A | * | 11/1988 | McComb et al. | ........... 356/382 |
| 5,495,334 A | * | 2/1996 | Nagoshi et al. | ............. 356/346 |
| 5,757,502 A | * | 5/1998 | Weling | ....................... 356/376 |
| 5,883,720 A | * | 3/1999 | Akiyama et al. | ........... 354/382 |

* cited by examiner

Primary Examiner—John Lee
Assistant Examiner—David A Vanore
(74) Attorney, Agent, or Firm—G. E. Ehrlich Ltd.

(57) ABSTRACT

The use of an intensity spectrum as a fingerprint to determine the layer structure of a semiconductor wafer product or partial product, thereby to determine the routing history of the product through a production line and prevent routing errors. Also, a production line having a plurality of successive stages for construction of a product such as a semiconductor wafer, and routers for transferring partly constructed product between the stages such that each stage receives a respective predefined partly constructed product as its input. The production line comprises: a predetermined intensity spectrum for at least one stage representing the respective part construction for the stage, an intensity spectrum deriver located at said at least one stage operable to obtain intensity spectra of incoming partly constructed product, and a comparator, for comparing said obtained intensity spectra with said predetermined intensity spectrum, to determine whether said incoming partly constructed products correspond with said respective predefined part construction for the stage.

36 Claims, 8 Drawing Sheets

METHOD AND APPARATUS FOR PRODUCTION LINE SCREENING

FIELD OF THE INVENTION

The present invention relates to a method and apparatus for production line screening and more particularly but not exclusively to screening of semiconductor wafer products at intermediate stages in a multi-tool semiconductor wafer production line.

BACKGROUND OF THE INVENTION

The semiconductor chip manufacturing process generally involves forming a silicon wafer and then carrying out a sequence of operations that essentially involves addition and selective removal of layers to build the functionality of the chip. The process may typically involve several hundred individual operations including deposition of dielectric and metal layers. Coating of photoresist, photolithography using a mask, etching of layers, ashing etc.

In a manufacturing production line, it is not untypical that something of the order of a thousand wafers may move together through the same sequence of operations at any one time using parallel paths amongst a set of tools. Different tools at different stages take different amounts of time to carry out their processes and thus it is generally found necessary to carry out intelligent routing operations to ensure maximum throughput of wafers. In any kind of routing operation, unless totally straightforward, there is a danger that a batch (or lot) of wafers are misrouted such that operations are carried out in the wrong sequence. Such misrouting leads to scrapping of the entire batch of wafers, generally a very expensive kind of an error just in terms of the batch alone. In addition, entering wafers into the wrong process tools at the wrong time can lead to damage of the process tool, for example due to contamination of the process chamber or the wafer breaking whilst inside the chamber and the like. Damage to the process tool may involve considerable down time, and a repair or replacement cost which is not inconsiderable.

At present the only solutions to routing errors lie in producing more effective and robust routing algorithms. For the vast majority of combinations of steps there is nothing on the wafers themselves that is available for a simple and rapid determination as to whether the wafer approaching a given tool has been through the correct preceding combination of steps.

PCT Patent Application No. WO 0012958 describes a measurement system known as TMS which uses light beams reflected from within layers of a wafer surface to make measurements of the thicknesses of transparent layers and in particular photoresist layers. The measurement is transformed typically into the frequency domain from which it is possible to determine the photoresist layer thickness very accurately. The measurement is quick but typically relates to the thickness or refractive index of a single transparent layer such as a photoresist layer, or to a set of thicknesses of a series of trenches but the system as described does not provide clear overall information that would enable a determination as to where the wafer is in the production line process.

SUMMARY OF THE INVENTION

It is an object of the embodiments hereinbelow to provide a solution to the above problem and to allow rapid and practical measurements to be made to a wafer to determine overall what layers it has and thus where it has been in the production process, from which it is possible to determine whether or not it is being correctly routed through the production process.

According to a first aspect of the present invention there is thus provided a production line having a plurality of successive stages for construction of a product comprising at least one layer on a substrate, and routers for transferring partly constructed products between the stages such that each stage receives a respective predefined partly constructed product as its input, the production line comprising:
 a predetermined reflected light intensity spectrum for at least one stage representing the respective predefined part construction for the stage,
 a reflected light intensity spectrum deriver located at said at least one stage operable to obtain reflected light intensity spectra of incoming partly constructed product, and
 a comparator, for comparing said obtained reflected light intensity spectra with said predetermined reflected light intensity spectrum, to determine whether said incoming partly constructed products correspond with said respective predefined part construction for the stage.

The production line preferably further comprises a routing error indicator operatively associated with said comparator for indicating a routing error when said spectra do not match.

The production line preferably further comprises a production interruption mechanism operatively associated with said routing error indicator for interruption of operation of said production line in the event of indication of a routing error.

Preferably, each stage comprises a plurality of production tools operating in parallel.

Preferably, each stage comprises a reflected light intensity spectrum deriver and has a predetermined intensity spectrum.

Preferably, said comparator is further operable to compare said obtained reflected light intensity spectrum with predetermined spectra of at least one other stage to reroute said product to said other stage if said spectra match.

Preferably, said production line is a semiconductor wafer production line for producing a layered semiconductor wafer product.

Preferably, said intensity spectrum deriver comprises
 an illuminator for irradiating a part product at at least one point thereof with a multiple wavelength radiation source,
 an intensity detector for detecting intensities within reflections of said source from said point,
 an analyzer operatively associated with said intensity detector for analyzing said intensities in terms of wavelength and converting said analyzed intensities spectrum into a frequency spectrum thereof, and
 a layer property determiner for determining, from said frequency spectrum, layer properties of layers on said part product.

Preferably, said property is one of a group comprising a thickness and a refractive index.

Preferably, said part product includes at least one at least partly transparent layer and said reflections include reflections from an upper and a lower surface of said at least partly transparent layer.

Preferably, said analyzer comprises a Fourier transform calculator for producing said frequency spectrum by Fourier transformation of said analyzed intensity spectrum.

According to a second aspect of the present invention there is provided a tool guard for restricting input to a production tool for carrying out a stage in the production of a layered product, the tool guard comprising:

a predetermined intensity spectrum representing an expected part construction for the stage, an intensity spectrum deriver located at said tool operable to obtain an intensity spectrum of an incoming partly constructed product, and a comparator, for comparing said obtained intensity spectrum with said predetermined intensity spectrum, to determine whether said incoming partly constructed product corresponds with said respective predefined part construction for the stage.

The tool guard preferably further comprises a routing error indicator operatively associated with said comparator for indicating a routing error when said spectra do not match.

The tool guard preferably further comprises a production interruption mechanism operatively associated with said routing error indicator for interruption of operation of said tool in the event of indication of a routing error.

Preferably, said tool is a semiconductor wafer production tool for use in a production line producing a layered semiconductor wafer product.

Preferably, said intensity spectrum deriver comprises an illuminator for irradiating a part product at at least one point thereof with a multiple wavelength radiation source, an intensity detector for detecting intensities within reflections of said source from said point, an analyzer operatively associated with said intensity detector for analyzing said intensities in terms of wavelength and converting said analyzed intensities into a frequency spectrum of the intensities, and a layer property determiner for determining, from said frequency spectrum, layer properties of layers on said part product.

Preferably, said property is one of a group comprising a thickness and a refractive index.

Preferably, said part product includes at least one at least partly transparent layer and said reflections include reflections from an upper and a lower surface of said at least partly transparent layer.

Preferably, said analyzer comprises a Fourier transform calculator for producing said frequency spectrum by Fourier transform of said analyzed intensities.

According to a third aspect of the present invention there is provided a production line router for routing intermediate inputs around a multiple stage production line, the intermediate inputs comprising substrates with at least one superimposed layer, the router comprising:

predetermined intensity spectra for each of a plurality of said stages representing a respective intermediate construction for the stage, at least one intensity spectrum deriver located within said production line for obtaining intensity spectra of intermediate inputs, a comparator, for obtaining a closest match between said obtained intensity spectrum and any of said predetermined spectra, said router being operable to route said intermediate input to a stage corresponding to said closest matching spectrum.

Preferably, each stage comprises a plurality of production tools operating in parallel.

Preferably, each stage comprises an intensity spectrum deriver and has a predetermined intensity spectrum.

Preferably, said production line is a semiconductor wafer production line for producing a layered semiconductor wafer product.

Preferably, said intensity spectrum deriver comprises an illuminator for irradiating a part product at at least one point thereof with a multiple wavelength radiation source, an intensity detector for detecting intensities within reflections of said source from said point, an analyzer operatively associated with said intensity detector for analyzing said intensities in terms of wavelength and converting said analyzed intensities into a frequency spectrum of the intensities spectrum, and a layer property determiner for determining, from said spectrum, layer properties of layers on said part product.

Preferably, said property is one of a group comprising a thickness and a refractive index.

Preferably, said intermediate input includes at least one at least partly transparent layer and said reflections include reflections from an upper and a lower surface of said at least partly transparent layer.

Preferably, said analyzer comprises a Fourier transform calculator for producing said spectrum by Fourier transform of said analyzed intensities.

According to a fourth aspect of the present invention there is provided a wafer production history determiner for determining the production history of a semiconductor wafer product, the determiner comprising:

a plurality of predetermined intensity spectra for semiconductor wafer products having completed respective stages of a multiple stage semiconductor wafer production process, an intensity spectrum deriver for obtaining an intensity spectrum of an incoming semiconductor wafer product, and a comparator, for comparing said obtained intensity spectrum with each of said predetermined intensity spectra, to determine a closest match between said obtained spectrum and one of said predetermined spectra, said determiner inferring said production history as including the respective completed stage corresponding to said closest match predetermined spectrum.

According to a fifth aspect of the present invention there is provided the use of a spectrum obtained by reflecting multiple wavelength light from a plurality of points on a layered product, to determine a production history of said layered product.

In a further aspect, in a production line having a plurality of successive stages for construction of a product comprising at least one at least semi-transparent layer on a substrate, and routers for transferring partly constructed product between the stages such that each stage receives a respective predefined partly constructed product as its input, and having a predetermined intensity spectrum associated with at least one stage representing the respective part construction for the stage, there is provided a method comprising:

obtaining intensity spectra of partly constructed products incoming to said stage, and comparing said obtained intensity spectra with said predetermined intensity spectrum, and thereby determining whether said incoming partly constructed product corresponds with said respective predefined part construction for the respective stage.

Preferably the method further comprises indicating a routing error when said spectra do not match.

Preferably the method further comprises interrupting operation of said production line in the event of indication of a routing error.

Preferably, each stage comprises a plurality of production tools operating in parallel.

Preferably the method further comprises obtaining intensity spectra for incoming partly constructed products to each stage, each said stage having a predetermined intensity spectrum.

Preferably the method further comprises comparing said obtained intensity spectrum with predetermined spectra of at least one other stage to reroute said product to said other stage if said spectra match.

Preferably, said production line is a semiconductor wafer production line for producing a layered semiconductor wafer product.

Preferably, obtaining said intensity spectrum comprises
  irradiating a part product at at least one point thereof with a multiple wavelength radiation source,
  detecting intensities within reflections of said source from said point,
  analyzing said intensities in terms of wavelength, thereby to produce a spectrum of intensities at respective wavelengths,
  converting said spectrum of intensities into a frequency spectrum, and
  determining, from said frequency spectrum, layer properties of layers on said part product.

Preferably, said property is one of a group comprising a thickness and a refractive index.

Preferably, said part product includes at least one at least partly transparent layer and said reflections include reflections from an upper and a lower surface of said at least partly transparent layer.

Preferably, said converting comprises producing said spectrum by Fourier transform of said analyzed intensities.

BRIEF DESCRIPTION OF THE DRAWINGS

For a better understanding of the invention and to show how the same may be carried into effect, reference will now be made, purely by way of example, to the accompanying drawings, in which.

DESCRIPTION OF THE PREFERRED EMBODIMENTS

As an introduction to the present invention, the measurement method of PCT Patent Application No. WO 0012958 is discussed in detail.

Figure 1A:
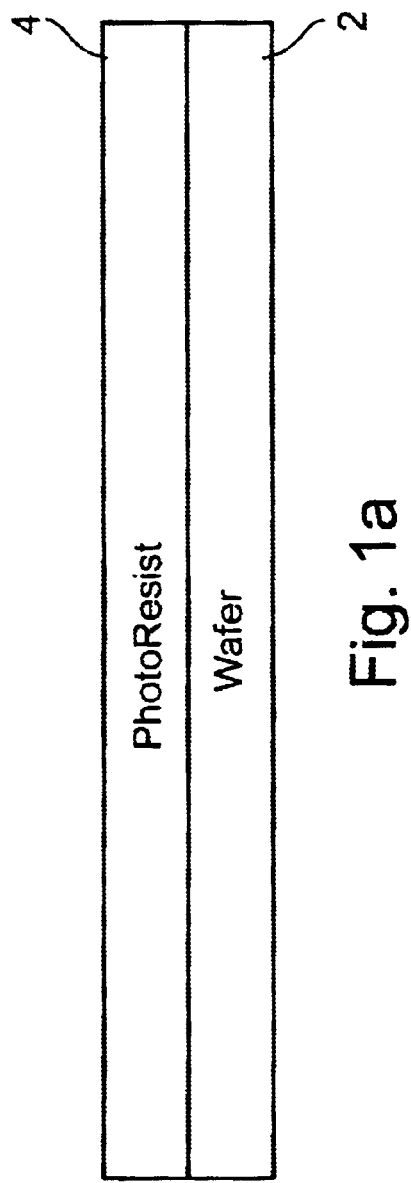
FIG. 1A is a simplified diagram of a layered wafer product.

Reference is now made to FIG. 1A, which is a simplified diagram showing a cross section of a silicon wafer at an intermediate stage in the production process. A silicon wafer 2 has a photoresist layer 4 attached thereon. In FIG. 1A the photoresist layer 4 is uniform and only a single measurement is necessary to determine the thickness of the layer.

Figure 1B:
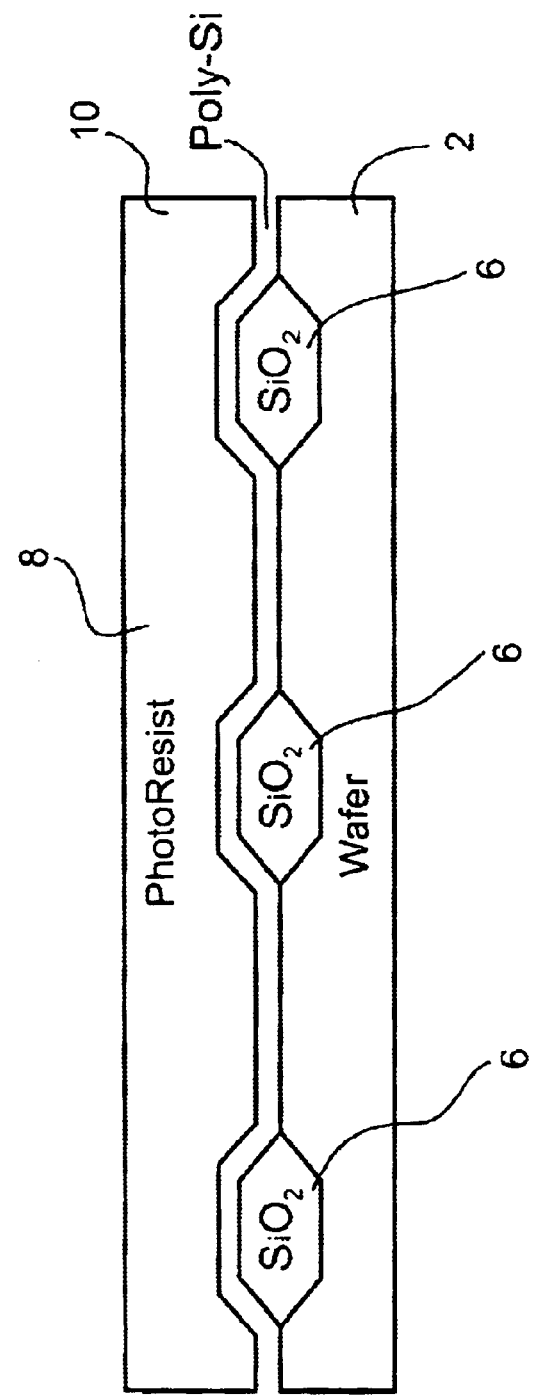
FIG. 1B is a simplified diagram of the layered wafer product of FIG. 1A at a later stage in the production process.

Reference is now made to FIG. 1B, which is a simplified diagram showing a cross section of another silicon wafer at another intermediate stage in the production process. In FIG. 1B the wafer 2 comprises a series of silicon dioxide structures 6, and a continuous polysilicon layer 8 covered by a photoresist layer 10. The TMS measurement system, as will be explained in more detail below, is particularly suitable for measuring the thickness of a transparent film. In the present case the photoresist layer 10 has differences in thickness at different places due to the silicon dioxide structures 6. There may thus be identified three different layer thickness $d_1$–$d_3$ in a typical wafer. The above differences in thickness are not accurately measurable in a conventional measurement system. The TMS system however, is capable of measuring such thickness variations in wafer layers that are applied or layers that have been removed, and furthermore the measurement is in situ and in real-time. The following description of the basic theory of operation of the TMS process will be helpful in understanding how this may be achieved.

Figure 2:
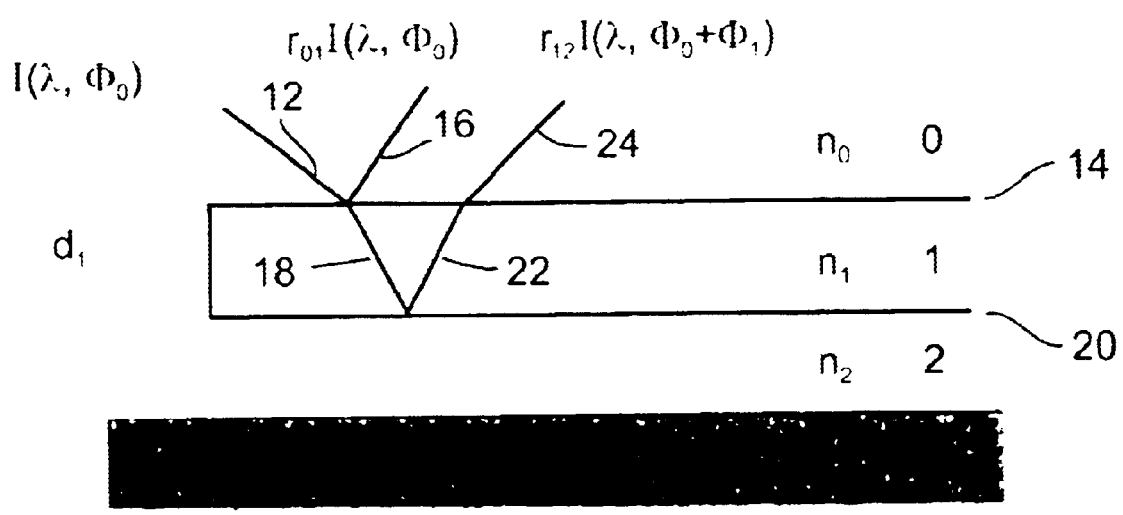
FIG. 2 is a simplified ray diagram illustrating how light reflection can be used to obtain information of layer thicknesses in a layered wafer product.

Reference is now made to FIG. 2, which is a simplified ray diagram showing incidence of light at an angle onto a series of layers having different refractive indices.

In FIG. 2, a material comprising three transparent layers, 0, 1, and 2, are subjected to light radiation. An incident ray 12 strikes a first layer boundary 14 to be split into a reflected ray 16 and a refracted ray 18. The refracted ray 18 strikes a second layer boundary 20 and is again split. This time only the reflected ray 22 is shown. As the refracted ray 22 strikes the first boundary 14 it is refracted again to comprise a third refracted ray 24.

Several methods are known for measuring thickness of transparent films using the reflected pattern of multi-wavelength light. When the beam shown in FIG. 2 is a monochromatic (single wavelength) light beam, and it arrives at a transparent film, part of the beam is reflected from the upper face (Layer 0/Layer 1 interface), and part is reflected from the bottom face (Layer 1/Layer 2 interface).

Expressing mathematically what is shown in FIG. 2:

$\lambda$ is the wavelength of the light;

$\phi_0$ is the phase angle of the incident light (and of the light reflected from the Layer 0/Layer 1 interface):

$\phi_0+\phi_1$ is the phase angle of the light reflected from the Layer 1/Layer 2 interface;

$r_{01}$ is the reflection coefficient of the Layer 0/Layer 1 interface;

$r_{12}$ is the reflection coefficient of the Layer 1/Layer 2 interfaces; and

I is the intensity of the incident light $$I = I_0 \cos(2\pi ct/\lambda + \phi_0) \tag{EQ. 1}$$

Where $I_0$ is the maximum intensity amplitude and c is the speed of light.

For light arriving perpendicularly at the film surface, the reflection coefficients from the top and bottom surfaces are:

$$r_{01}(n_1-n_0)/(n_1+n_0) \; r_{12}\,(n_2-n_1)/(n_2+n_1) \tag{EQ. 2}$$

wherein $n_0, n_1, n_2$ are the refractive indices of layers 0, 1 and 2, respectively.

The light reflected from the upper face interferes with the light reflected from the bottom face, giving an overall reflection coefficient (R) which is a function of the layer thickness and the layer refractive index. This reflection can be described by the, well-known, Frenel equation.

$$R=(r_{01}^2+r_{12}^2+2r_{01}r_{12}\cos 2\Phi_1)/(1+r_{01}^2r_{12}^2+2r_{01}r_{12}\cos 2\Phi_1) \tag{EQ. 3}$$

where:

$$\Phi_1=2\pi n_1 d_1/\lambda \tag{EQ. 4}$$

where:

$d_1$—layer thickness.

Illuminating the film with multi-wavelength light (white light), and measuring the reflectance at each wavelength ($\lambda$), gives R as a function of $\lambda$, i.e., $R(\lambda)$.

Illuminating a product wafer having a complex (i.e. laterally varying) topography with a large spot of multi-wavelength light causes a reflected beam which is a composition of the separate reflection of each of the thicknesses taken alone.

$$R(\lambda,d_1,\ldots,d_n) \Sigma_1(r_{(i-1),i}^2+r_{i(i+1)}^2+\\ 2r_{(i-1),i}r_{i(i-1)}\cos 2\Phi_1)/(I^4 r_{(i-n)}^2 r_{(i-1)}^2+$$

$$2_{(i-1),i}r_{i(i+1)}\cos 2\Phi_1) \tag{EQ. 5}$$

By simple mathematical operations it is possible to express the reflection coefficient by:

$$R(\lambda,d_1,\ldots,d_n)=\Sigma_i[1-\lambda_i/(1+B\cos(2\Phi_i))] \tag{EQ. 6}$$

where:

$$\lambda_i=(1-r_{(i-1),i}^2)(1-r_{i(i+1)}^2)/(1+r_{(i-1),i}^2 r_{i(i+1)}^2)$$

and $$B_i=2r_{(i-1),i}r_{i(i+1)}/(1+r_{(i-1),i}^2 r_{i(i+1)}^2)$$

Applying ways of frequency decomposition of the reflection coefficient may provide each of the arguments ($\Phi_1$) and from Eq 3 & 4 it is possible to determine the layer thickness assuming that the layer refractive index is known. Alternatively it is possible to determine the layer refractive index, if the layer thickness is known.

There are several ways to perform frequency decomposition, some of which are suggested below:

Mathematical Decompositions

1) The family of orthogonal transform methods, for example Fourier transforms,
2) The family of methods based on the maximum likelihood principle,
3) The family of methods based on parametric models
4) The family of subspace decomposition methods.

Electrical Decomposition:

Electrical frequency filters are widely used in electrical systems. Such filters serve to define windows in the frequency domain and output the amplitude of the component of the input signal within the range of the window. Passing the reflected signal (translated into electrical signal) through a set of filters or a single filter with variable frequency gives the desired decomposition.

Figure 3:
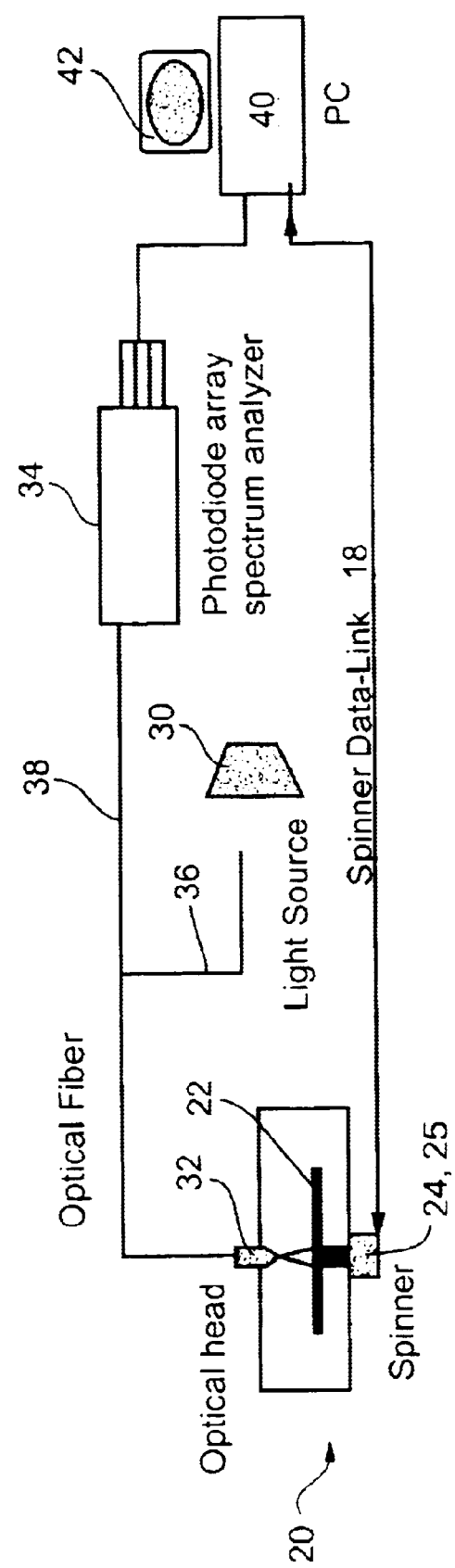
FIG. 3 is a simplified schematic diagram of a reflection-based measuring device associated with a spinner in a semiconductor wafer production line.

Reference is now made to FIG. 3, which is a simplified block diagram showing an arrangement for measuring the thickness variations of a transparent layer on a semiconductor substrate. The measurement arrangement is mounted on a photoresist coating track. The coating track comprises a spinning bowl 20. The spinning bowl 20 comprises a spinner chuck 22 for receiving a wafer W, and a motor 24 having an encoder 25, for rotating the chuck, and the wafer thereon, while a photoresist applicator (not shown) dispenses photoresist material at the center of the wafer. The wafer W is first rotated at a low speed as photoresist material is dispensed at its center, and then is rotated at high speed (e.g., 300–5000 rpm) by electric motor 24, which produces centrifugal forces causing the photoresist liquid to flow towards the edge of the wafer W. Most of the photoresist (e.g. about 95%) is spilled off the wafer and is collected in a bowl (not shown)to be drained later, while the adhesion forces between the wafer surface and the photoresist hold smaller amounts of the photoresist as a coating on the wafer. As briefly described earlier, the final thickness of the photoresist coating is produced when a balance is achieved between the centrifugal forces, the adhesion to the surface, and the shear forces caused by the viscosity of the photoresist liquid. During the spinning process the solvent contained in the photoresist evaporates and the viscosity increases. Thus, a final thickness is reached which is also a function of the solvent evaporation rate, and is affected by the temperature, air flow and other environmental conditions.

As illustrated in FIG. 3, the apparatus further includes an illuminating device 30 for illuminating the photoresist coating with a beam of light of multiple wavelengths (white light), and a detector 32 for detecting the intensity of the light reflected from the photoresist coating for each wavelength. Preferably, the detector 32 is connected to a photodiode array spectrum analyzer. The spectrum analyzer is able to detect interference patterns over a range of wavelengths and, using the equations as given above, is able to obtain data of the layer thickness.

In order to obtain information on the thickness or refractive index of more then one spot on the wafer, multiple detecting heads 32 may be placed at different locations above the wafers. The outputs of the detecting heads 32 are preferably multiplexed for sending to the spectrum analyzer 34, for example by mechanically switching between each of the optical fibers. Data acquisition is thus enabled from different sites on the wafer.

The illuminating device preferably applies a beam of white light in any suitable manner, e.g., via an optical fiber 36, to the optical head 32 mounted above the wafer W, thereby projecting a beam of light onto the photoresist coating of the wafer W as the wafer is rotated. The light reflected from the photoresist coating is directed in any suitable manner, e.g., via another optical fiber 38, to the spectrum analyzer 34, thereby to detect the intensity of the light reflected from the photoresist coating for each wavelength.

The outputs of the spectrum analyzer 34 are preferably fed to a processor 40 which processes the outputs according to the basic theory of operation described above, and displays the outputs on a screen 42. In addition, an output of processor 40 may also be used, for example as a feedback input, for controlling the application of the photoresist coating 8 onto the wafer W.

Preferably, the optical head 32 is mounted for movement along the radial axis, to enable the optical head to be located at any selected radius of the wafer W under test. During the wafer rotation the angular position of the wafer is identified by the encoder 25, which, combined with the radial position, gives the location of a desired measurement spot on the wafer. Preferably, the beam of light 13 is large enough to cover at least one complete die of a plurality of dies carried by the wafer W. The use of such a beam of light large enough to cover a complete die, or a multiple thereof, provides a number of advantages. For example it better ensures that the combined reflected light detected by detector 15 will not change substantially between measurements, irrespective of the difference in the exact measurement position. Furthermore, the large spot size increases the signal collected by the optical head and also increases the speed of detection.

Figure 4:
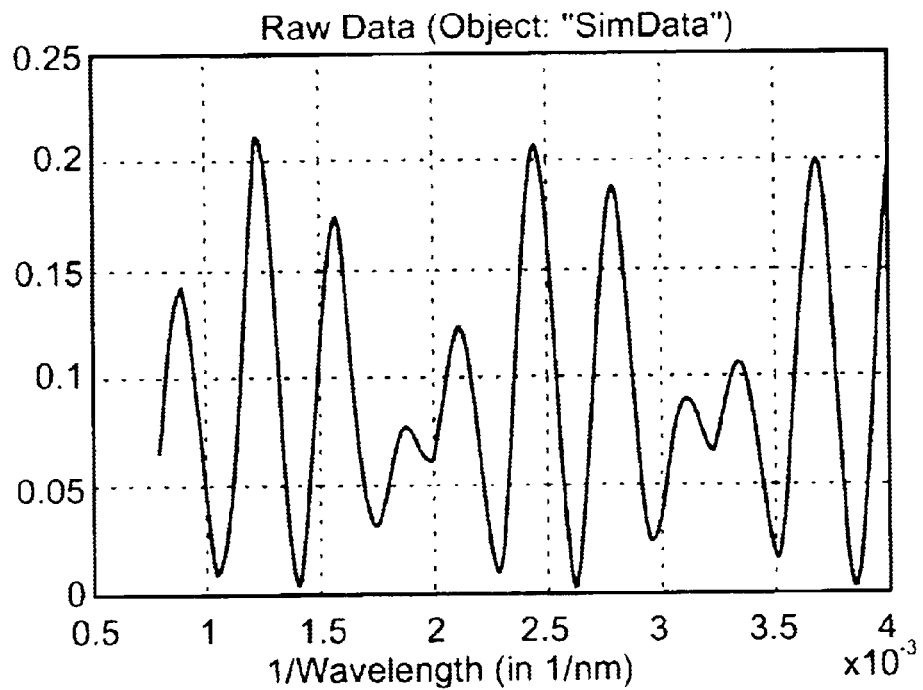
FIG. 4 is a typical graph of inverse wavelength against intensity obtained by measuring a semiconductor wafer using the apparatus of FIG. 3.

Reference is now made to FIG. 4, which is a simplified graph illustrating inverse wavelength against amplitude for a typical set of measurements involving a simulation of the above-described process when applied to a wafer coated with a photoresist coating having two different thicknesses ($d_1$, $d_2$) at different points, for example as the result of an etching operation. FIG. 4 thus illustrates the sum R of the reflectance coefficients $r_1$ and $r_2$ as a function of thickness $d_1$ and $d_2$ respectively and the wavelength. In the example, $d_1=0.95\mu$; $d_2=1.25\mu$, and the ratio of the intensity of the separated signals=1.

Figure 5:
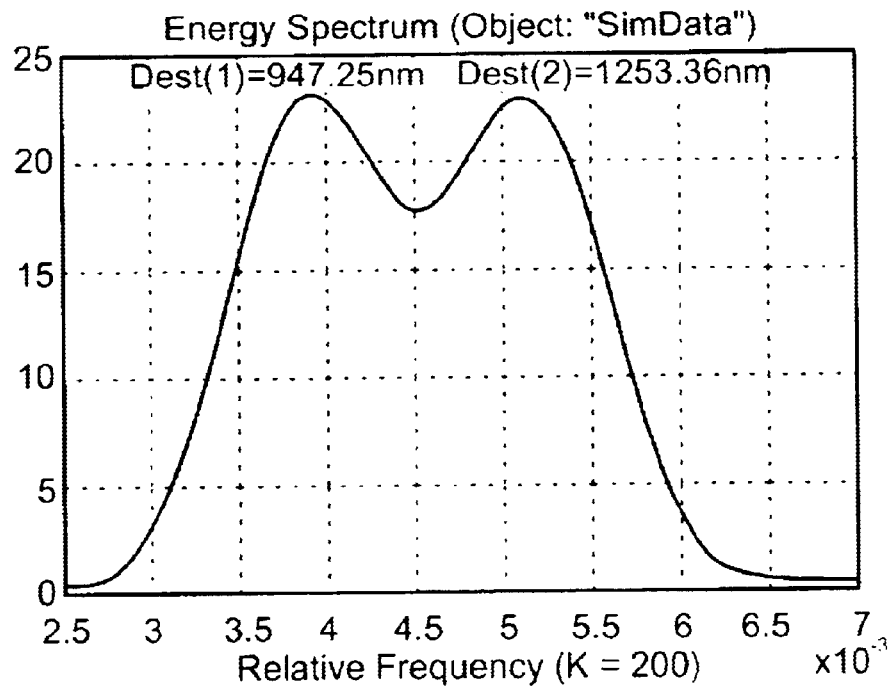
FIG. 5 is the energy or intensity spectrum obtained by performing a Fourier transform on the graph of FIG. 4.

Reference is now made to FIG. 5 which is a simplified graph showing the data of FIG. 4 to which a Fourier transform has been applied, that is to say a Fourier transform is applied to the signal R which defines the overall reflection. The Fourier transform produces a series of Fourier coefficients for the signal frequencies, from which the thickness of the transparent film can be determined for each respective signal frequency. As shown in FIG. 5, the two thicknesses of the photoresist coating produce two quite distinct peaks, each representing the frequency related to one of the thicknesses.

Figure 6:
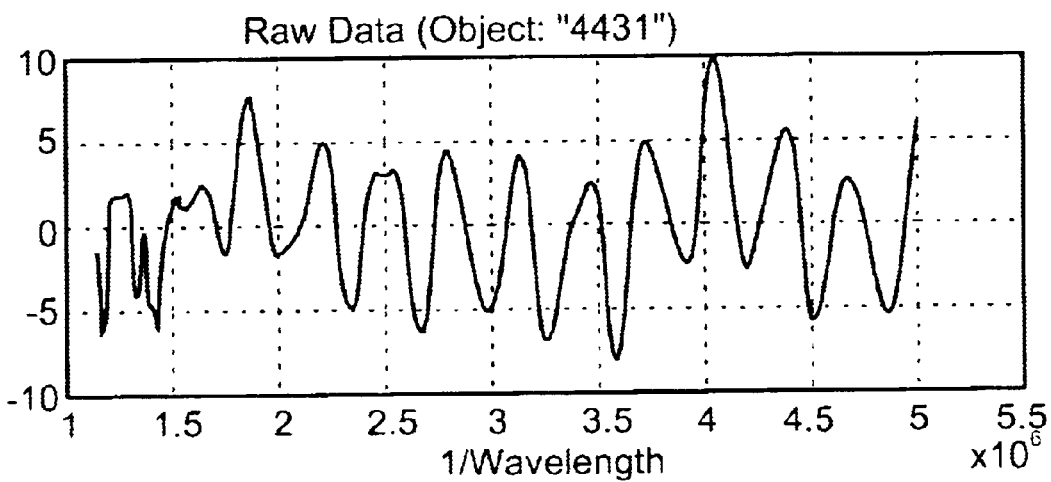
FIG. 6 is a typical graph of wavelength against intensity for another semiconductor wafer.
Figure 7:
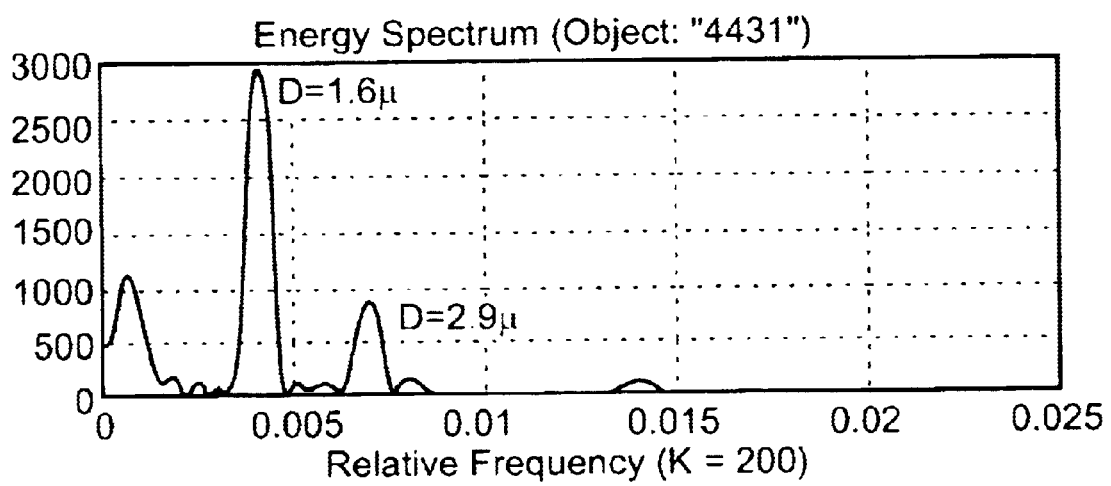
FIG. 7 is the energy or intensity spectrum obtained by performing a Fourier transform on the graph of FIG. 6.

Reference is now made to FIGS. 6 and 7, which are simplified graphs illustrating how the system described above may be used to measure thicknesses of two layers superimposed upon each other.

FIG. 6 shows intensity against wavelength for a reflection signal from a wafer with a pattern of metal lines covered by an inter-metal dielectric on Silicon dioxide (Oxide). Two thicknesses of oxide are present at the vicinity of a measurement spot:

1) oxide on top of the metal lines, with $d_2=1556$ nm, and
2) oxide on top of previously deposited dielectric of thickness of $d_1=722$ nm. FIG. 7 illustrates the signal received after processing by a frequency transformation process similar to that mentioned above. The results show the peaks at frequencies related to $d_2$ and $d_1+d_2$.

Figure 8:
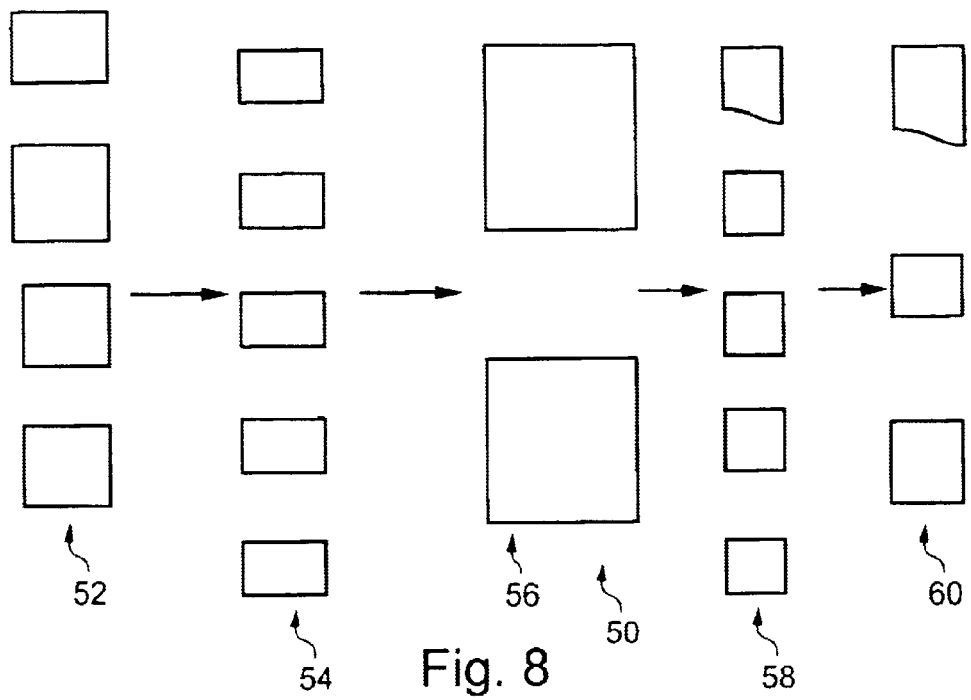
FIG. 8 is a simplified schematic diagram of a part of a production line comprising numerous tools arranged as a series of stages, each stage comprising a plurality of tools in parallel.

Reference is now made to FIG. 8, which is a simplified diagram illustrating a length 50 of a production line for producing semiconductor wafers. In production line length 50, five stages 52–60 of a production process are carried out by sets of tools operating in parallel. The different stages each have different numbers of tools, typically because the tools at each stage operate at different rates. Thus to achieve a given wafer throughput requires four tools at a first stage 52, five tools at a second stage 54, two tools at a third stage 56, five tools at a fourth stage 58 and three tools at a fifth stage 60.

Wafers are routed between stages, in batches of 25 wafers (lots), typically by robot shuttles or conveyor arrangements, or by human operators. Any lot finishing a given stage is preferably routed to the next available tool in the next stage. For certain production runs one or more of the stages may not be needed and certain of the tools may be down for maintenance at any given time. Thus routing of wafers amongst the tools is not a trivial problem.

For each stage of the production process, a wafer that has been correctly routed will already have a given configuration of layers. A measurement device as described above may thus be placed at the input to each tool or each stage to obtain a Fourier transform indicating layer thicknesses in the wafer. Provided that the transform shows the expected number of peaks indicating the expected frequencies, the wafer is admitted to the respective stage of the process. If a wafer arrives at a particular stage and a Fourier transform is obtained indicating an unexpected layer configuration then a routing error is inferred and the wafer is not admitted to the respective stage of the process.

It is noted at this point that a deep layer history is only possible with transparent or semi-transparent layers. However surface information at least can be obtained even in the case of opaque layers.

In the event of a routing error, the Fourier transform is generally sufficient to indicate the routing history of the wafer so that the wafer can be reinserted at the correct point in the process, as will be explained in more detail below.

Figure 9:
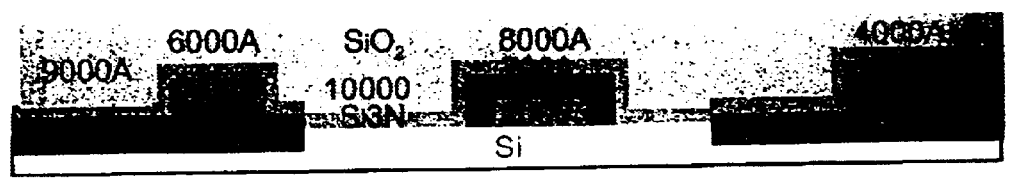
FIG. 9 is a simplified cross-section of a wafer that could typically be constructed by the production line of FIG. 8.

Reference is now made to FIG. 9, which is a simplified cross section of a semiconductor wafer at an intermediate stage in a wafer production process. The cross-section comprises numerous layers and numerous different thicknesses and refractive index which may be expected to appear in the transform.

Figure 10:
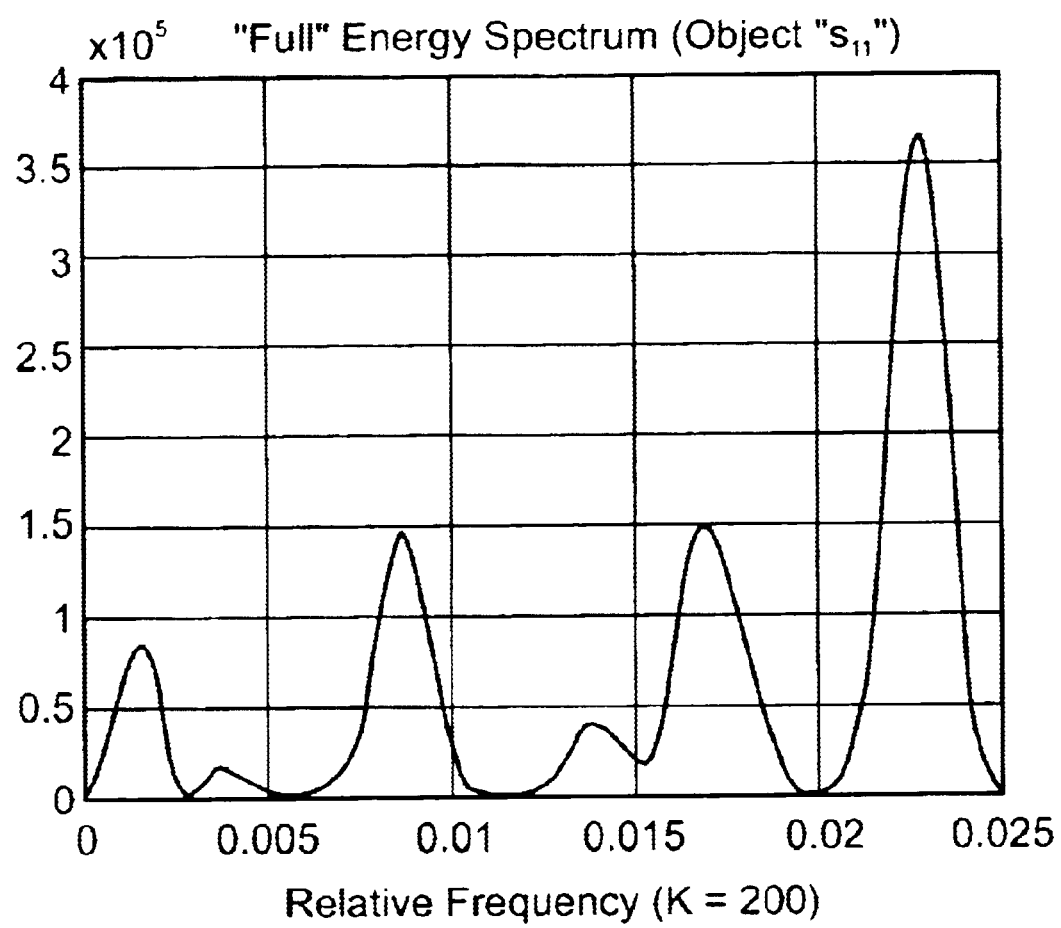
FIG. 10 is an intensity spectrum obtained from the wafer of FIG. 9.

Reference is now made to FIG. 10, which is a simplified graph of the Fourier transform of the thickness measurement carried out on the wafer of FIG. 9. The transform is essentially an energy spectrum of the light falling on the wafer and provides a fingerprint as to the layer structure of the wafer. The spectrum of FIG. 10 can be compared manually or electronically with an expected spectrum to determine whether a routing error has or has not occurred.

Comparison between spectra may be carried out automatically using pattern matching or other image analysis techniques or even by simple measurements of peak levels, which may then be compared statistically.

The optical thickness (or refractive index) measurement is simple and rapid to make and thus does not slow down production throughput.

In the event of a routing error the process may be shut down or the wafers rerouted. Rerouting may be carried out automatically by comparing the spectra indicated in the routing error with spectra expected at other stages in the process. The wafers are then rerouted to a stage given a spectral match.

A production line according to an embodiment of the present invention may have successive stages for construction of a product, such as a semiconductor wafer product. The wafer product typically has one or more transparent or semi-transparent layers on a substrate, the layers being added at certain stages of the production process and removed or selectively removed at other stages such that each stage of the production process is characterised by a given set of layer thicknesses on the wafer surface.

The production line, as mentioned above, preferably comprises routers for transferring partly constructed product between the stages. Preferably each stage should receive a part product having a given previous production history so that each stage is reached by the wafers in a given sequence.

One or more of the stages is supplied with a predetermined intensity spectrum corresponding to the respective part construction or production history for the stage, The stages are additionally supplied with an intensity spectrum deriver for obtaining intensity spectra of incoming partly constructed wafers arriving at the stage. The deriver may be a single device supplied for the entire stage or several such devices may be provided, in particular if the stage comprises several tools operating in parallel.

A comparator is additionally supplied for comparing the obtained intensity spectra with the predetermined intensity spectrum, to determine whether the incoming partly constructed products correspond with the respective predefined part construction for the stage. The comparison may be carried out using, for example, pattern matching techniques.

If the spectra do not match then a routing error indicator preferably indicates a routing error (miss-process).

In a preferred embodiment a production interruption mechanism is connected with the routing error indicator to interruption operation of the production line in the event of indication of a routing error. Thus it is possible to automatically prevent insertion of semiconductor wafers into the wrong part of the process.

In another preferred embodiment, in the event of a failure to match, the comparator is further operable to compare the obtained intensity spectrum with predetermined spectra of other stages. The wafer can then be automatically rerouted to any other stage giving a spectral match. The embodiment is thus usable as an automatic rerouter.

It will be appreciated that as well as carrying out spectral matching automatically, spectral matching can be carried out manually. Additionally or alternatively, decisions on rerouting or on interrupting the process may be made manually.

Preferably, and as discussed above, the intensity spectrum deriver comprises the following features:

1) an irradiator or illuminator for irradiating a wafer at one or points thereon with a multiple wavelength radiation source, typically white light,
2) an intensity detector for detecting intensities of reflections of the irradiation,
3) an analyzer operatively connected to the intensity detector for analyzing the intensities in terms of wavelength and converting the analyzed intensities into a frequency spectrum, and
4) a layer property determiner for determining, from the spectrum, layer properties of layers on the part product. The layer property is typically a thickness or a refractive index, the spectrum typically showing each thickness around the points measured as a separate peak.

The analyzer may include comprises a Fourier transform calculator for producing the spectrum by Fourier transform of the analyzed intensities.

The above described arrangement may be provided at an individual tool to serve as a tool guard for restricting input to the tool.

The above-described arrangement may be provided at each tool or at each stage of a production line or part thereof to serve as an automatic or semiautomatic production line router for routing intermediate inputs around a multiple stage production line.

The above-described arrangement may alternatively be provided, perhaps independently of a production line, as a wafer production history determiner for determining the production history of a semiconductor wafer product. The history determiner is useful as a process diagnostic tool, for example by a process or control engineer. The history determiner is supplied with a series of spectra, each relating to different stages in the production process and wafers are compared with the series of spectra to obtain a closest match, thereby to determine their production history.

Figure 11:
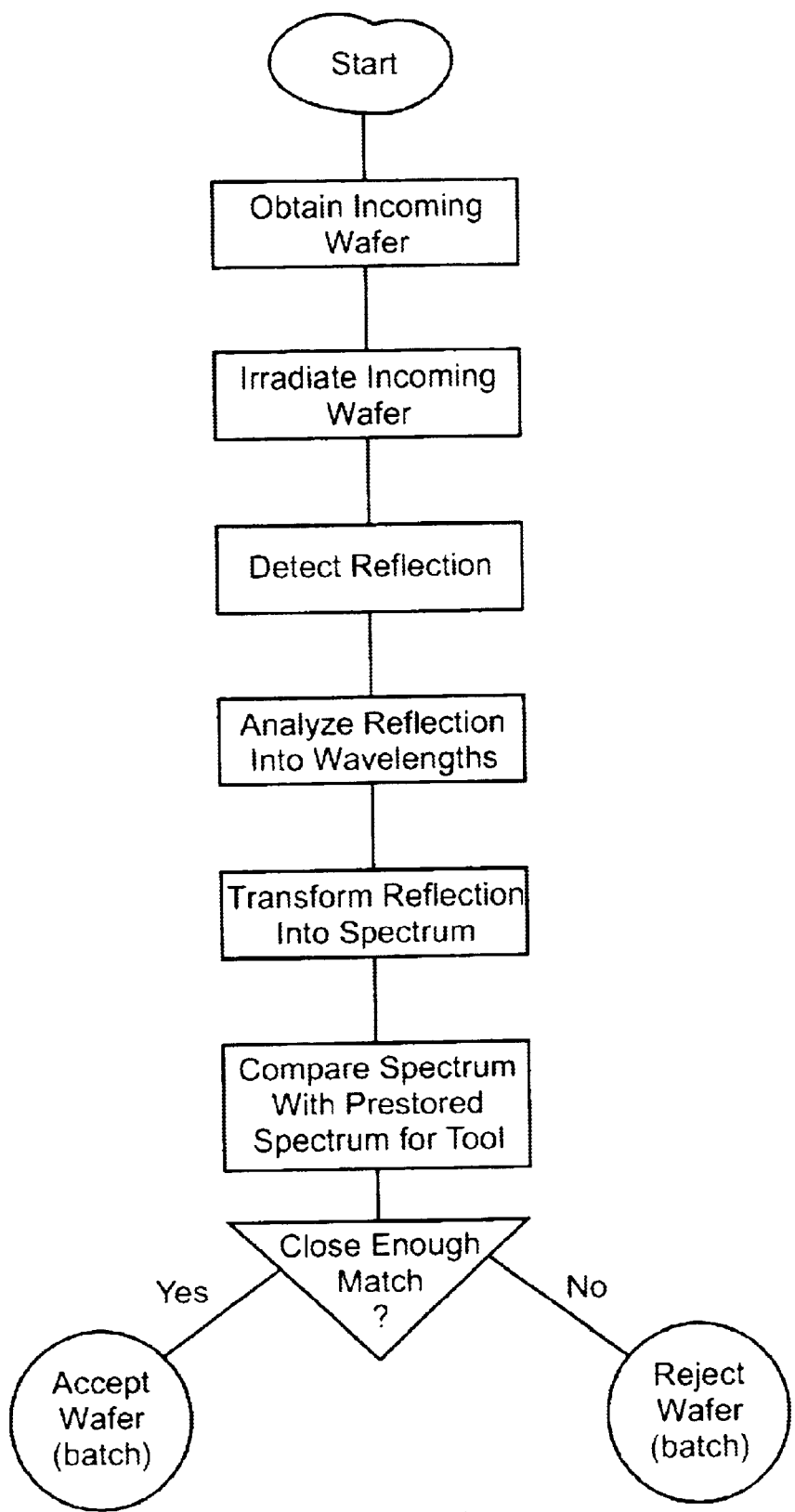
FIG. 11 is a simplified flow chart illustrating operation at a single tool of the routing mechanism of a preferred embodiment of the present invention.

Reference is now made to FIG. 11, which is a simplified flow chart showing operation of the wafer acceptance arrangement at a given tool or stage in the production line. An incoming wafer is obtained and irradiated at several points using multiple wavelength light. The light for each of the points is detected and analyzed into separate wavelengths, preferably using the analyzer described above. The analyzed data are then transformed, preferably using Fourier analysis, to produce a frequency domain spectrum.

The spectrum obtained as described above may then be compared with the prestored intensity spectrum associated with the respective tool or stage. The comparison may be automatic, involving pattern matching or any other suitable technique or it may be manual and the result of the comparison may be used to determine whether the incoming wafer should be accepted or rejected by the respective tool or stage.

In an embodiment rejecting the incoming wafer comprises indicating a routing error when the spectra do not match. Alternatively or additionally, rejecting the incoming wafer may involve interrupting operation of the production line in the event of indication of a routing error.

Preferably, each stage has its own predetermined intensity spectrum.

In one embodiment, following rejection of a wafer at a given tool an additional step may be provided of comparing the obtained intensity spectrum with predetermined spectra of other stages to reroute the wafer to whichever of the other stages gives a match.

According to the above embodiments there is thus provided use of an intensity spectrum as a 'fingerprint' to determine the layer structure of a semiconductor wafer product or partial product, thereby to determine the routing history of the product through a production line and prevent routing errors.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

What is claimed is:

1. A production line having a plurality of successive stages for construction of a product comprising plurality of layer thicknesses on a substrate, and routers for transferring partly constructed products between the stages such that each stage receives a respective predefined partly constructed product as its input, the production line comprising:

predetermined layers properties data for at least one stage representing the respective predefined part construction for the stage, a reflected light intensity spectrum deriver located at said at least one stage operable to obtain reflected light intensity spectra of incoming partly constructed product, said intensity spectrum deriver comprising:

an illuminator for irradiating a part product at least one point thereof with a multiple wavelength radiation source, an intensity detector for detecting intensities within reflections of said source from said point, an analyzer operatively associated with said intensity detector for analyzing said intensities in terms of wavelength, converting said analyzed intensities spectrum into a frequency spectrum thereof and carrying out orthogonal processing of said frequency spectrum, said analyzer comprising:

a spectral analyzer connected to an output of said intensity illuminator for providing a spectral analysis of said intensities and an orthogonal transform calculator connected to an output of said spectral analyzer for carrying out an orthogonal transformation of said spectrally analyzed intensities, thereby to reveal thickness information of individual layers, a layer property determiner for determining, from said orthogonal transformation of said frequency spectrum, layer properties of layers on said part product, and a comparator, for comparing said obtained orthogonal transformation of said frequency spectrum or layer property data derived therefrom with expected layer properties, to determine whether layers of said incoming partly constructed products correspond with layers defined in said respective predefined part construction for the stage.

2. A production line according to claim 1, further comprising a routing error indicator operatively associated with said comparator for indicating a routing error when said layers do not match.

3. A production line according to claim 2, comprising a production interruption mechanism operatively associated with said routing error indicator for interruption of operation of said production line in the event of indication of a routing error.

4. A production line according to claim 1, wherein each stage comprises a plurality of production tools operating in parallel.

5. A production line according to claim 4, wherein each stage comprises a reflected light intensity spectrum deriver and a layer property determiner and has a predetermined intensity spectrum and predetermined layer properties.

6. A production line according to claim 5, wherein said comparator is further operable to compare said obtained layer properties with layer properties of at least one other stage to reroute said product to said other stage if layers indicated in said spectra match.

7. A production line according to claim 5, wherein said production line is a semiconductor wafer production line for producing a layered semiconductor wafer product.

8. A production line according to claim 1, wherein said property is one of a group comprising a thickness and a refractive index.

9. A production line according to claim 1, wherein said part product includes at least one at least partly transparent layer and said reflections include reflections from an upper and a lower surface of said at least partly transparent layer.

10. A production line according to claim 1, wherein said orthogonal transform calculator comprises a Fourier transform calculator for producing said frequency spectrum by Fourier transformation of said analyzed intensity spectrum.

11. A tool guard for restricting input to a production tool for carrying out a stage in the production of a layered product having a plurality of later thickness values, the tool guard comprising:

predetermined layers properties data representing an expected part construction for the stage, an intensity deriver located at said tool operable to obtain an intensity spectrum of an incoming partly constructed product, said intensity spectrum deriver comprising:

an illuminator for irradiating a part product at at least one point thereof with a multiple wavelength radiation source, and an intensity detector for detecting intensities within reflections of said source from said points, an analyzer operatively associated with said intensity deriver for analyzing said intensities in terms of wavelength and converting said analyzed intensities spectrum into a transformation of a frequency spectrum thereof, said analyzer comprising:

a spectral analyzer for carrying out a spectral analysis of said detected intensities to produce an intensity spectrum, and an orthogonal transform calculator, associated with said spectral analyzer, for carrying out said orthogonal transformation of said analyzed intensity spectrum, a layer property determiner, associated with said analyzer, for determining, from said orthogonal transformation of said frequency spectrum, layer properties of layers on said part product, and a comparator, for comparing layer property determiner output with said predetermined layers properties data to determine whether layer properties of said incoming partly constructed product corresponds with layer properties of said respective predefined part construction for the stage.

12. A tool guard according to claim 11, further comprising a routing error indicator operatively associated with said comparator for indicating a routing error when said layer properties do not match.

13. A tool guard according to clam 12, comprising a production interruption mechanism operatively associated with said routing error indicator for interruption of operation of said tool in the event of indication of a routing error.

14. A tool guard according to claim 11, wherein said tool is a semiconductor wafer production tool for use in a production line producing a layered semiconductor wafer product.

15. A tool guard according to claim 11, wherein said property is one of a group comprising a thickness and a refractive index.

16. A tool guard according to claim 11, wherein said part product include at least one at least partly transparent layer and said reflections include reflections from an upper and a lower surface of said at least partly transparent layer.

17. A tool guard according to claim 11, wherein said orthogonal transform calculator comprises a Fourier transform calculator for producing said frequency spectrum by Fourier transform of said analyzed intensities.

18. A production line router for routing intermediate inputs around a multiple stage production line, the intermediate inputs comprising substrates with at least one superimposed layer, the router comprising:

predetermined layers properties data for each of a plurality of said stages representing a respective intermediate construction for the stage, at least one intensity deriver located within said production line for obtaining intensity spectra of intermediate inputs, said intensity spectrum deriver comprising:

an illuminator for irradiating a part product at at least one point thereof with a multiple wavelength radiation source, an intensity detector for detecting intensities within reflections of said source from said point, an analyzer operatively associated with said intensity detector for analyzing said intensities in terms of wavelength and converting said analyzed intensities spectrum into a frequency spectrum thereof, said analyzer comprising:

a spectrum analyzer, associated with said intensity detector for obtaining a spectral analysis of said intensities, and an orthogonal transform calculator, associated with said spectrum analyzer, for applying an orthogonal transformation to said intensity spectrum, a layer property determiner, associated with said orthogonal transform calculator, for determining, from said orthogonal transformation of said frequency spectrum, layer properties of layer on said part product, and a comparator, for obtaining a closest match between layers defined in said obtained intensity spectrum and layers defined in any of said predetermined layer properties data, said router being operable to route said intermediate input to a stage corresponding to said closest matching spectrum.

19. A production line router according to claim 18, wherein each stage comprises a plurality of production tools operating in parallel.

20. A production line router according to claim 19, wherein each stage comprises an intensity spectrum deriver and a layer property determiner and has a predetermined intensity spectrum and predetermined layer properties.

21. A production line router according to claim 18, wherein said production line is a semiconductor wafer production line for producing a layered semiconductor wafer product.

22. A production line router according to claim 18, wherein said property is of a group comprising a thickness and a refractive index.

23. A production line router according to claim 18, wherein said intermediate input includes at least one at least partly transparent layer and said reflections include reflections from an upper and a lower surface of said at least partly transparent layer.

24. A production line according to claim 18, wherein said orthogonal transform calculator comprises a Fourier transform calculator for producing said spectrum by Fourier transform of said analyzed intensities.

25. A water production history determiner for determining the production history of a semiconductor wafer product having multiple thicknesses, the determiner comprising:

a plurality of predetermined layer properties data for semiconductor wafer products having completed respective stages of a multiple stage semiconductor wafer production process, an intensity deriver for obtaining an intensity spectrum of an incoming semiconductor wafer product said intensity spectrum deriver comprising:

an illuminator for irradiating a part product at at least one point thereof with a multiple wavelength radiation source, and an intensity detector for detecting intensities within reflections of said source from said point, an analyzer operatively associated with said intensity detector for analyzing said intensities in terms of wavelength and converting said analyzed intensities spectrum into a transformation of frequency spectrum thereof, said analyzer comprising:

a spectrum analyzer associated with said intensity detector tin performing a spectral analysis of said intensities, and an orthogonal transform calculator, associated with said spectrum analyzer, for carrying out orthogonal transformation of said analyzed intensity spectrum, a layer property determiner for determining, from said orthogonal transformation of said frequency spectrum, layer properties of layers on said part products, and a comparator, for comparing layers defined in said obtained layers properties with layers defined in each of said predetermined layers properties data, to determine a closest match between said obtained layers properties and one of said predetermined layers properties data, said determiner inferring said production history as including the respective completed stage corresponding to said closest match predetermined layers properties data.

26. A method of production history analysis for a layered product having multiple laser thicknesses and at least one discontinuous layer, comprising:

applying orthogonal transform processing to an intensity spectrum obtained by reflecting multiple wavelength light from a plurality of points on said layered product, using a result of said orthogonal transform processing to determine layer thicknesses including a thickness of said discontinuous layer within said product, and using said layer thicknesses to determine a production history of said layered product.

27. In a production line having a plurality of successive stages for construction of a product comprising a plurality of layer thickness values on a substrate, and routers for transferring a partly constructed product between the stages such that each stage receives a respective predefined partly constructed product as its input, and having a predetermined intensity spectrum associated with at least one stage representing the respective part construction for the stage, a method comprising:

obtaining intensity spectra of partly constructed products incoming to said stage, said obtaining comprising irradiating a part product at least one point thereof with a multiple wavelength radiation source, detecting intensities within reflections of said source from said point, analyzing said intensities in terms of wavelength, thereby to produce a spectrum of intensities at respective wavelengths, transforming said spectrum of intensities into a frequency spectrum using orthogonal transformation of said spectrum of intensities, determining, from said orthogonal analysis of said frequency spectrum, layer properties of layers on said part product, and comparing said layer properties with layer properties of said predetermined intensity spectrum and thereby determining whether said incoming partly constructed product corresponds with said respective predefined part construction for the respective stage.

28. A method according to claim 27, further comprising indicating a routing error when said layer properties do not match.

29. A method according to claim 28, comprising interrupting operation of said production line in the event of indication of a routing error.

30. A method according to claim 27, wherein each stage comprises a plurality of production tools operating in parallel.

31. A method according to claim 30, comprising obtaining intensity spectra for incoming partly constructed products to each stage, each said stage having a predetermined intensity spectrum defining layer properties.

32. A method according to claim 31, comprising comparing said obtained layer properties with predetermined layer properties of at least one other stage to reroute said product to said other stage if respective layer properties match.

33. A method according to claim 27, herein said production line is a semiconductor wafer production line for producing a layered semiconductor wafer product.

34. A method according to claim 27, wherein said property is one of a group comprising a thickness and a refractive index.

35. A method according to claim 27, wherein said part product includes at least one at least partly transparent layer and said reflections include reflections from an upper and a lower surface of said at least partly transparent layer.

36. A production line according to claim 27, wherein said orthogonal analysis comprises Fourier analysis.

* * * * *